United States Patent [19]

Maya

[11] Patent Number: 5,023,213

[45] Date of Patent: * Jun. 11, 1991

[54] PRECURSORS IN THE PREPARATION OF TRANSITION METAL NITRIDES AND TRANSITION METAL CARBONITRIDES AND THEIR REACTION INTERMEDIATES

[75] Inventor: Leon Maya, Oak Ridge, Tenn.

[73] Assignee: United States Department of Energy, Washington, D.C.

[*] Notice: The portion of the term of this patent subsequent to May 24, 2005 has been disclaimed.

[21] Appl. No.: 939,920

[22] Filed: Dec. 9, 1986

[51] Int. Cl.$^5$ .............. C04B 35/58; C07F 7/00; C07F 9/00; C07F 11/00

[52] U.S. Cl. .................................. 501/96; 556/1; 556/43; 556/46; 556/52; 556/58; 556/70; 556/87; 556/112; 556/121; 556/137; 556/140; 556/176

[58] Field of Search .............. 501/96; 423/413; 556/42, 43, 51, 52, 57, 58, 1, 46, 70, 87, 112, 121, 137, 140, 176

[56] References Cited

U.S. PATENT DOCUMENTS

| | | | |
|---|---|---|---|
| 2,264,812 | 12/1941 | Schulze | 556/57 |
| 2,459,966 | 1/1947 | Schilling | 556/57 |
| 2,579,413 | 12/1951 | Boyd | 556/51 |
| 3,239,565 | 3/1966 | Kreevoy et al. | 556/57 |
| 3,373,177 | 3/1968 | Young | 556/57 |
| 3,615,271 | 10/1971 | Dietz | 556/51 |
| 3,933,971 | 1/1976 | Baucom | 423/54 |
| 4,029,747 | 6/1977 | Merkl | 423/413 |
| 4,042,610 | 8/1977 | Manzer | 556/58 |
| 4,175,109 | 11/1979 | Kim | 423/54 |
| 4,196,178 | 4/1980 | Iwai et al. | 423/413 |
| 4,746,501 | 5/1988 | Maya | 556/43 |

FOREIGN PATENT DOCUMENTS

| | | | |
|---|---|---|---|
| 68700 | 6/1978 | Japan. | |
| 151280 | 8/1985 | Japan | 501/96 |

OTHER PUBLICATIONS

Chemical Abstracts citation 84:46655e.
Chemical Abstracts citation 84:11692n.
Interrante et al., "Studies of Organometallic Precursors to Aluminum Nitride," Abstract of Materials Research Society Meeting; Apr. 1986, at Palo Alto, Calif.

*Primary Examiner*—Wayne A. Langel
*Attorney, Agent, or Firm*—Katherine P. Lovingood; Stephen D. Hamel; William R. Moser

[57] ABSTRACT

A process for making ammonolytic precursors to nitride and carbonitride ceramics. Extreme reaction conditions are not required and the precursor is a powderlike substance that produces ceramics of improved purity and morphology upon pyrolysis.

9 Claims, No Drawings

PRECURSORS IN THE PREPARATION OF TRANSITION METAL NITRIDES AND TRANSITION METAL CARBONITRIDES AND THEIR REACTION INTERMEDIATES

This invention is a process for preparing ceramic nitrides and carbonitrides from ammonolytic intermediates that produce powder ceramic materials which are easy to use in manufacturing articles. The invention was developed pursuant to a contract with the United States Department of Energy.

BACKGROUND OF THE INVENTION

Advanced ceramic materials are chemically inert compounds with high thermal stability and mechanical strength. Such characteristics make these materials attractive candidates for applications such as heat engines, cutting tools, and turbine blades, articles which are presently made with expensive super alloys. Current interest in advanced ceramics centers around such materials as carbides, nitrides, borides, and silicides which have properties of hardness, corrosion resistance, and thermal stability that cannot be matched by metallic alloys or other structural materials. Examples of these ceramic materials are SiC, $Si_3N_4$, TiC, TiN, VC, WC, and BN. Other nitrides and carbonitrides are useful as superconducting materials and include NbN, MoN, and $Nb(C,N,)$.

Although chemical inertness of advanced ceramics is an advantage in these applications, it makes fabrication of components through pressing and sintering a difficult task and places stringent demands on the purity and morphology of the starting materials. Previously, these compounds were prepared by a very high temperature reaction in a nitrogen atmosphere using metal oxide or pure metal powder and carbon as reactants. The reaction yielded clumps of product material that had to be ground into a powder before it could be used. Not only are the high temperature reaction and grinding steps difficult and costly processes, they can also be a serious source of contamination.

More recently, attempts have been made to make metal nitrides by reacting the transition metal halides with ammonia or a nitrogen and hydrogen gas mixture. The ammonia or nitrogen atmosphere not only provides the reactant for making the nitride, but it also assures the absence of oxygen which can cause damage of the final ceramic product if it is present during the reaction. However, when titanium chloride was reacted with ammonia at 1000° C., the titanium nitride product was in the form of hard clumps that required grinding before they could be used, and there was also a hydrogen chloride by-product which is reactive and corrosive to the ceramic material.

Such problems have led researchers to attempt to develop appropriate precursors that can be converted to ceramic materials by chemical means requiring less rigorous conditions and producing a product that is in a more readily usable form. This accomplishment would be an important development in the area of ceramic production.

SUMMARY OF THE INVENTION

In view of the above needs, it is an object of this invention to provide a process for making ceramics using readily available materials and moderate reaction conditions.

It is also an object of this invention to provide a process for making ceramics that results in a product that is in a readily usable form and does not produce reactive by-products.

It is a further object of this invention to provide precursors for the process for making ceramics.

Another object of this invention is to provide a process for making ceramics that is fast and provides good yields.

It is also an object of this invention to provide ceramics that are pure and in fine particulate form. Upon further study of the specifications and appended claims, further objects and advantages of this invention will become apparent to those skilled in the art. The organometallic amide is a composition having a transition metal bound to an inorganic amide or imide ligand or ligands, and having acetylide ligands, either terminal or bridging, also bound to the transition metal. To achieve the forgoing and other objects in accordance with the purpose of the present invention, the composition of this invention may comprise a precursor to a transition metal nitride that is an organometallic amide of a transition metal. The invention is also a process for making ceramics and comprises pyrolyzing the precursor to produce the nitride or carbonitride.

Among the many advantages of forming ceramics in this way includes a reaction that proceeds at moderate conditions, formation of fine particulate precursors of high metal content resulting in minimum shrinkage upon pyrolysis, and a very pure ceramic with controlled carbon content.

DETAILED DESCRIPTION OF THE PREFERRED EMBODIMENT

The preparation of advanced ceramic materials requires, in general, the exclusion of oxygen since the presence of this element can have detrimental effects on the properties of some ceramics. Thus, the use of oxygen-free reactants and solvents is almost a necessity in the preparation of precursors. For this reason, liquid ammonia is a useful reaction medium for conducting this type of synthetic chemistry. Titanium halides were chosen as convenient starting materials since they are readily available and exhibit a high degree of purity. Previous work has been done on titanium chloride at high temperatures of about 1000° C. with ammonia. The reaction required about two days and resulted in a titanium nitride solid mass of material in the form of clumps that was difficult to handle without further processing. In addition to the unfavorable morphology of the ceramic material, the reaction also produced a reactive and corrosive by-product hydrogen chloride.

At room temperature, titanium IV underwent ammonolytic reactions in liquid ammonia to yield essentially $TiX(NH_2)_3 \cdot 2NH_3$; however, this reaction required several days due to a competing reverse reaction and produced an ammonium halide by-product which was not easily separated from the titanium haloamide. In attempts to promote the reaction and prevent a reverse reaction, alkali metal borohydride was added to react with the ammonium halide byproduct. The products of this side reaction, an alkali halide salt and aminoborohydride, were soluble in liquid ammonia and easily washed away from the solid primary product, a transition metal haloamide. The success of using the borohydride to block the reverse reaction was the first step in the development of the process of this invention.

The transition metal haloamides were treated with a carbon salt or an amide salt depending on whether the carbonitride or the pure nitride was desired. The carbon salt must be one that will attach to the transition metal and remove the halogen by formation of a halide salt. A suitable carbon salt is sodium acetylide which produces a transition metal acetylide derivative. Such compounds comprise the precursor to the ceramic carbonitride.

An advantage to forming ceramics using this process is that the carbon content of the carbonitride can be controlled since the carbon of the carbon salt replaces the halogen of the transition metal haloamide; therefore, the greater the number of halogen molecules in the transition metal halide, the higher the carbon content of the final ceramic will be.

To be more specific, the precursors are made by starting with a halide of a transition metal such as vanadium, tungsten, molybdenum, titanium, or niobium which is mixed with an alkali metal borohydride such as potassium borohydride or sodium borohydride, or other suitable borohydrides, in liquid ammonia at room temperature. The reaction, ammonolysis, is a parallel reaction to hydrolysis $$MX_n + 2xNH_3 \rightarrow MX_{n-x}(NH_2)_x + xNH_4X$$

where M is a transition metal, X is a halogen, and n and x are variables. The side reaction of a borohydride of an alkali metal, such as potassium, with the ammonium halide by-product prevents a reverse reaction.

$$NH_4X + KBH_4 \rightarrow KX + NH_4BH_4$$

$$NH_4BH_4 \rightarrow NH_3BH_3 + H_2 \uparrow$$

These by-products are soluble in liquid ammonia and washed away.

The insoluble metal haloamide is then reacted with a carbon salt of a metal that will attach to the halide of the metal haloamide producing an insoluble organometallic amide and soluble metal halide salt. Sodium acetylide is a good choice for the carbon salt.

$$M_nX_{n-x}(NH_2)_x + (n-x)NaC \equiv CH \rightarrow M_n(C \equiv CH)_{n-x}(NH_2)_x + (n-x)NaX$$

The product of this reaction is a composition having an acetylide ligand attached to the transition metal. It is clear the acetylide is attached to the metal because it substitutes for the halogen that was previously attached to the metal. Therefore, the product of such a reaction is a compound having a transition metal bound to inorganic amide or imide ligands, and having acetylide ligands, either terminal or bridging, also bound to the transition metal. Since the number of carbon atoms is in direct relation to the number of halogens of the metal haloamide, the carbon content of the carbonitride can be controlled. For example, one can begin with either $TiBr_4$ to form $TiBr(NH_2)_3$ or $TiBr_3$ to form $TiBr_2(NH_2)$. $TiBr(NH_2)_3$ reacts with $NaC \equiv CH$ to yield a $Ti_4(C \equiv CH)(NH)_6NH_2$ precursor, whereas $TiBr_2(NH_2)$ reacts with $NaC \equiv CH$ to yield $Ti_4(C \equiv C)_2(NH)_4$, a precursor with twice the carbon content as the preceding one. Generically, the organometallic amide can be characterized as $M^n(C \equiv CH)_x(NH_2)_{n-x}$ where n is the oxidation state of the metal and x is a variable. The resulting organometallic amide is the precursor to the final ceramic which is obtained by pyrolyzing the precursor at about 800° C. under a dynamic vacuum to give a fine pure powder that is in readily usable form.

If the nitride is desired instead of the carbonitride, then the metal haloamide is reacted with an amide salt of a metal that will attach to the halide. Depending on which halogen comprises the metal haloamide, the suggested salt can be either potassium amide or sodium amide, the potassium being suitable for bonding to a bromine and sodium suitable for chlorine. For example, to make the titanium nitride, a titanium haloamide such as $TiBr(NH_2)_3$ is reacted with $KNH_2$ to produce $KTi(NH_2)_2$ which upon pyrolysis gives the powdered ceramic TiN product.

EXAMPLE

A heavy walled ampoule was loaded with 2.17 mmole of $NbBr_5$ and 11.8 mmole $KBH_4$. Eleven grams of ammonia was condensed in the ampoule which was then sealed. After standing overnight at room temperature, the ampoule was opened and it was found that a reaction had taken place producing 4.24 mmole $H_2$/mmole of Nb and a brown precipitate, the ammonolytic product, containing 70% of the initial niobium. The precipitate had a composition corresponding to $NbBr(NH_2)_2NH$. When this material was treated with $NaC \equiv CH$ in liquid ammonia, it produced a derivative having a composition corresponding to $Na_4Nb_6(C \equiv C)_4(N)_8NH$. Pyrolysis of the derivative at 800° C. under vacuum resulted in a 30% weight loss and left a residue identified by its x-ray diffraction pattern as niobium carbonitride. Chemical analysis of this material revealed the composition to be 88.4% Nb, 4.4% C, 6.1% N, 0.1% Br and 1.0% Na

I claim:
1. A composition comprising:
   a transition metal bound to;
   a first ligand selected from the group inorganic amide and imide ligands; and
   a second ligand being acetylide ligands.
2. The composition of claim 1 wherein said acetylide ligand is terminal.
3. The composition of claim 1 wherein said acetylide ligand is bridging between said transition metal molecules.
4. The composition of claim 1 wherein said transition metal is selected from the group vanadium, tungsten, molybdenum, titanium and niobium.
5. The precursor of claim 1 having the formula $M^n(C \equiv CH)_x(NH_2)_{n-x}$ wherein M is a transition metal and n is the oxidation state of M and x is a variable.
6. A process for making ceramics comprising: pyrolyzing the precursor of claim 1 in an inert atmosphere.
7. A process for making ceramics comprising: pyrolyzing the precursor of claim 2 in an inert atmosphere.
8. A process for making ceramics comprising: pyrolyzing the precursor of claim 3 in an inert atmosphere.
9. A process for making ceramics comprising: pyrolyzing the precursor of claim 4 in an inert atmosphere.

* * * * *